United States Patent [19]

Ohmae et al.

[11] Patent Number: 5,208,016
[45] Date of Patent: May 4, 1993

[54] ANTIMICROBIAL SUBSTANCE AND ANTIMICROBIAL RESIN COMPOSITION CONTAINING ETHYLENE COPOLYMER

[75] Inventors: Tadayuki Ohmae, Chiba; Takashi Chinuki, Osaka; Tadashi Sakurai, Osaka; Kouichiro Asao, Osaka; Makoto Fujimura, Osaka; Shigeo Yamamoto, Hyogo; Masato Mizutani, Osaka; Tomohiro Teramae, Hyogo, all of Japan

[73] Assignee: Sumitomo Chemical Co., Ltd., Osaka, Japan

[21] Appl. No.: 318,310

[22] Filed: Mar. 3, 1989

[30] Foreign Application Priority Data

Mar. 3, 1988 [JP] Japan .................................. 63-50867
Apr. 27, 1988 [JP] Japan ................................. 63-107009

[51] Int. Cl.$^5$ ................. A61K 31/78; 31/765
[52] U.S. Cl. ................. 424/78.27; 424/78.35; 424/78.37; 523/122
[58] Field of Search ............ 526/307; 424/81, 78, 424/78.27, 78.35, 78.37; 525/385, 355; 523/122

[56] References Cited

U.S. PATENT DOCUMENTS

| | | | |
|---|---|---|---|
| 3,308,081 | 3/1967 | Glabisch et al. | 526/307 |
| 4,526,932 | 7/1985 | Imazaki et al. | |
| 4,647,589 | 3/1987 | Valone. | |
| 4,708,870 | 11/1987 | Pardini | 424/81 |
| 4,831,095 | 5/1989 | Ohmae et al. | 526/307 |

FOREIGN PATENT DOCUMENTS

| | | | |
|---|---|---|---|
| 367473 | 3/1967 | Switzerland. | |
| 887900 | 1/1962 | United Kingdom | 526/307 |
| 1185283 | 3/1970 | United Kingdom. | |

*Primary Examiner*—Thurman K. Page
*Assistant Examiner*—P. Kulkosky
*Attorney, Agent, or Firm*—Sughrue, Mion, Zinn, Macpeak & Seas

[57] ABSTRACT

An antimicrobial substance containing an ethylene copolymer as an active ingredient and an antimicrobial resin composition containing the ethylene copolymer are disclosed. The ethylene copolymer comprises from 40 to 95% by weight of ethylene, from 5 to 60% by weight of at least one dialkylaminoalkylacrylamide comonomer represented by formula (I):

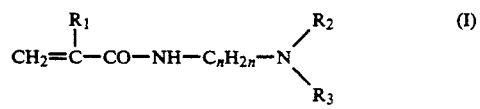

wherein $R_1$ represents a hydrogen atom or a methyl group: $R_2$ and $R_3$, which may be the same or different, each represents an alkyl group having from 1 to 4 carbon atoms; and n represents an integer of from 2 to 5, and up to 20% by weight of one or more of other ethylenically unsaturated comonomers, and has a number average molecular weight of from 5,000 to 50,000.

8 Claims, No Drawings

ANTIMICROBIAL SUBSTANCE AND ANTIMICROBIAL RESIN COMPOSITION CONTAINING ETHYLENE COPOLYMER

FIELD OF THE INVENTION

This invention relates to an antimicrobial substance containing an ethylene copolymer having antimicrobial activity as an active ingredient and an antimicrobial resin composition comprising a thermoplastic resin and the ethylene copolymer.

BACKGROUND OF THE INVENTION

Techniques for endowing resin molded articles, fibrous resin products or synthetic paper products with antimicrobial activity include compounding of organic chemicals or metallic compounds having antimicrobial activity, e.g., compounds of copper, silver or zinc, into resins; and post-treatment of fiber or paper with chemicals as described in JP-A-62-184126, JP-A-62-250277, JP-A-59-66578, and JP-A-59-164342 (the term "JP-A" as used herein means an "unexamined published Japanese patent application").

The organic chemicals to be compounded into resins frequently involve problems of poor heat stability, toxicity, harmfulness, and short-duration.

The metallic ions having antimicrobial activity, when merely incorporated into resins, are liable to fall off the resin products during use and are therefore of short duration. In order to solve this problem, it has been proposed that metallic ions having antimicrobial activity are supported on inorganic solid particles having ion exchange ability, e.g., zeolite, and then the solid particles are incorporated into the resin as disclosed in JP-A-59-133235, JP-A-62-195037, and JP-A-62-195038. This technique is, however, disadvantageous, particularly when applied to production of fibrous products, in that the particle size of the inorganic solid particles should be small enough to maintain satisfactory spinnability, which would increase the cost and deteriorate dispersibility in the resin during the incorporation process.

SUMMARY OF THE INVENTION

In order to overcome the above-described problems associated with the conventional biocides for resins, the inventors have conducted extensive investigations and, as a result, it has now been found that a copolymer of ethylene and a dialkylaminoalkylacrylamide comonomer exhibits excellent biocidal activity.

The present invention relates to an antimicrobial substance containing, as an active ingredient, an ethylene copolymer comprising from 40 to 95% by weight of ethylene, from 5 to 60% by weight of at least one dialkylaminoalkylacrylamide comonomer represented by formula (I):

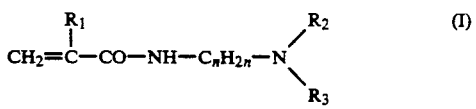

wherein $R_1$ represents a hydrogen atom or a methyl group; $R_2$ and $R_3$, which may be the same or different, each represents an alkyl group having from 1 to 4 carbon atoms; and n represents an integer of from 2 to 5, and up to 20% by weight of one or more of other ethylenically unsaturated comonomers, said ethylene copolymer having a number average molecular weight of from 5,000 to 50,000.

Implicit in the ethylene copolymer of the present invention are an aqueous dispersion of a cationic polymer obtained by reacting the above-described ethylene copolymer with hydrochloric acid in water to form a quaternary salt and then addition-reacting an epihalohydrin compound with the quaternary salt, and the above-described ethylene copolymer having incorporated therein metallic ions.

DETAILED DESCRIPTION OF THE INVENTION

The ethylene copolymer, metallic ion-containing ethylene copolymer, and aqueous dispersion of a cationic polymer of the ethylene copolymer in accordance with the present invention are capable of controlling phytopathogenic bacteria and industrially harmful microorganisms. Examples of the phytopathogenic microorganism on which the antibiocidal substance of the present invention is effective and the plant disease caused by the respective bacterium are shown below.

| Phytopathogenic Microorganism | Plant Disease |
| --- | --- |
| Pyricularia oryzae | blast of rice plant |
| Cochliobolus miyabeanus | helminthosporium leaf spot of rice plant |
| Rhizoctonia solani | sheath blight of rice plant |
| Gibberella fujikuroi | Bakanae disease of rice plant |
| Gibberella zeae | scab of wheat (barley) |
| Typhula sp., Micronectriella nivalis | typhula snow blight of wheat (barley) |
| Pseudocercosporella herpotrichoides | eyespot disease of wheat and barley |
| Rhynchosporium secalis | scald of barley |
| Septoria tritici | speckled leaf blotch of wheat |
| Pyrenophora graminea | leaf stripe of barley |
| Leptosphaeria nodorum | glume blotch of wheat |
| Diaporthe citri | melanosa of citrus |
| Elsinoe fawcetti | scab of citrus |
| Penicillium digitatum | common green mold of citrus |
| Penicillium italicum | blue mold of citrus |
| Xanthomonas citri | canker of citrus |
| Sclerotinia mali | blossom blight of apple |
| Valsa mali | canker of apple |
| Alternaria mali | alternaria leaf spot of apple |
| Venturia inaequalis | scab of apple |
| Agrobacterium tumefaciens | crown gall of apple |
| Venturia nashicola | scab of pear |
| Alternaria kikuchiana | black spot of pear |
| Gymnosporangium haraeanum | rust of pear |
| Sclerotinia cinerea | brown rot of peach |
| Cladosporium carpophilum | scab of peach |
| Phomopsis sp. | phomopsis rot of peach |
| Elsinoe ampelina | anthracnose of grape |
| Glomerella cingulata | ripe rot of grape |
| Gloeosporium kaki | anthracnose of persimmon |
| Cercospora kaki | angular leaf spot of persimmon |
| Mycosphaerella nawae | circular leaf spot of persimmon |
| Colletotrichum lagenarium | anthracnose of cucumber |
| Mycosphaerella melonis | gummy stem blight of cucumber |
| Pseudomonas lachrymans | bacterial leaf spot of cucumber |
| Alternaria solani | early blight of tomato |
| Cladosporium fulvum | leaf mold of tomato |
| Phomopsia vexans | brown spot of egg plant |
| Alternaria japonica | alternaria leaf spot of crucifer |
| Cercosporella brassicae | white spot of crucifer |

-continued

| Phytopathogenic Microorganism | Plant Disease |
|---|---|
| Puccinia allii | rust of onion |
| Pseudomonas syringae | bacterial leaf spot of onion |
| Erwinia carotovora | bacterial rot of onion |
| Cercospora kikuchii | purple speck of soybeans |
| Elsinoe glycines | sphaceloma scab of soybeans |
| Disporthe phascolorum var. sojae | pod and stem blight of soybeans |
| Colletotrichum lindemuthianum | anthracnose of kidney beans |
| Mycosphaerella personatum | leaf spot of peanut |
| Cercospora arachidicola | leaf spot of peanut |
| Alternaria solani | early blight of potato |
| Exobasidium reticulatum | net blister blight of tea |
| Elsinoe leucospila | scab of tea |
| Alternaria longipes | brown spot of tobacco |
| Colletotrichum tabacum | anthracnose of tobacco |
| Cercospora beticola | leaf spot of beat |
| Alternaria radicina | alternaria black rot of beat |
| Diplocarpon rosae | black spot of rose |
| Septoria chrysanthemiindici | leaf blight of chrysanthemum |
| Botrytia cinerea | gray mold in various plants |
| Sclerotinia sclerotiorum | sclerotinia rot in various plants |
| Rhizoctonia solani, phythium sp. | damping-off of various plants |

Examples of the industrially harmful microorganism on which the biocide of the present invention is effective are as follows: Aspergillus sp., Chaetomium sp., Cladosporium sp., *Staphylococcus aureus, Escherichia coli,* Rhizopus sp., Aurebasidium sp., Mucor sp., Penicillium sp., Bacillus sp., Enterobacter sp., Pseudomonas sp., Saccharomyces sp., Candida sp., *Fusarium moniliforme,* and Trichoderma sp.

Therefore, the ethylene copolymer inclusive of the metallic ion-containing ethylene copolymer and the cationic polymer aqueous dispersion according to the present invention is useful as an active ingredient of pesticides for plants or seeds; biocides for microorganism harmful to industrial products such as woods, bamboo goods, fibrous goods, paper goods, cosmetics, glass goods, coatings, and synthetic resins; sanitary processing agents, detergents or preservatives; and biocides for non-medical use, e.g., slime controlling agents and food preservatives.

The process for producing the ethylene copolymer of the invention is not particularly limited, and generally effected by a so-called high-pressure polyethylene process. That is, ethylene and an acrylamide comonomer are copolymerized under a pressure of from 500 to 3,000 kg/cm$^2$ at a temperature of from 100° to 300° C. in the presence of a radical polymerization initiator. The polymerization reaction can be carried out in a batchwise, semi-continuous, or continuous system. To an industrial advantage, a continuous high-pressure process is preferred.

For the purpose of facilitating continuous and stable feeding of the dialkylaminoalkylacrylamide comonomer to a high-pressure polymerization system by means of a pump or for the purpose of increasing softness of the resulting copolymer, ethylene and the acrylamide copolymer may further be combined, if desired, with at least one other ethylenically unsaturated comonomer which is copolymerizable with ethylene. In this case, the ethylenically unsaturated comonomer used is copolymerized in a copolymerization ratio of up to 20%, preferably up to 15%, by weight. Preferred examples of the ethylenically unsaturated comonomer are methyl acrylate, ethyl acrylate, methyl methacrylate, vinyl acetate, dimethylaminoethyl methacrylate, and dimethylaminoethyl acrylate.

Specific examples of the dialkylaminoalkylacrylamide comonomer of formula (I) which can be preferably used in this invention include dimethylaminoethylacrylamide, dimethylaminopropylacrylamide, dimethylaminobutylacrylamide, diethylaminoethylacrylamide, diethylaminopropylacrylamide, diethylaminobutylacrylamide, di-n-propylaminoethylacrylamide, di-n-propylaminopropylacrylamide, di-n-propylaminobutylacrylamide, N-(1,1-dimethyl-3-dimethylaminopropyl)acrylamide, and N-(2-methyl-3-dimethylaminopropyl)acrylamide, and methacrylamide derivatives corresponding to these acrylamide derivatives.

Preferred of them are dimethylaminopropylacrylamide, diethylaminopropylacrylamide, dimethylaminoethylacrylamide, and diethylaminoethylacrylamide, and the corresponding methacrylamides.

The proportion of the dialkylaminoalkylacrylamide comonomer unit in the ethylene copolymer ranges from 5 to 60%, preferably from 15 to 55%, and more preferably from 20 to 50%, by weight.

The number average molecular weight of the ethylene copolymer falls within the range of from 5,000 to 50,000, preferably from 8,000 to 40,000, as measured by gel-permeation chromatography (GPC) in a tetrahydrofuran solution using polystyrene whose molecular weight is known as a standard. If the number average molecular weight is less than 5,000, the copolymer resin has a low strength and finds difficulty in uniform kneading with other resins. If it exceeds 50,000, the resin also finds difficulty in forming a uniform dispersion with other resins.

The ethylene copolymer can be easily melt-mixed with thermoplastic resins, such as poly-$\alpha$-olefins (e.g., polyethylene and polypropylene), chlorine-containing resins (e.g., polyvinyl chloride), polyesters, and polyamides, to thereby provide a biocidal resin composition. In this case, the ethylene copolymer is used in an amount of from 0.1 to 50 parts by weight, preferably from 1 to 30 parts by weight, per 100 parts by weight of the thermoplastic resin. If the amount of the ethylene copolymer is less than 0.1 part by weight, the biocidal activity attained is not sufficient. If it exceeds 50 parts by weight, the characteristics inherent to the thermoplastic resin are impaired, or processability of the resin composition is deteriorated.

While the ethylene copolymer of the invention exhibits satisfactory biocidal activity by itself, its biocidal activity can be further improved and stably sustained by incorporating a metallic ion exhibiting biocidal activity, e.g., a silver ion, a copper ion, and a zinc ion, through absorption or mixing.

The amount of the biocidal metallic ion to be incorporated into the ethylene copolymer is subject to variation depending on the end use but is preferably not more than 5% by weight. If it is more than 5% by weight, there arise problems, such as changes of physical properties of the resin.

Incorporation of the metallic ion into the ethylene copolymer can easily be achieved by melt-mixing a thermoplastic resin and the ethylene copolymer, processing the mixture into films, sheets, fibers, woven fabric, non-woven fabric, molded articles, and the like and soaking the products in an aqueous solution of the intended metal salt. In some applications involving a dyeing process, dyeing and metallic ion absorption may be achieved simultaneously by incorporating the metallic ion into a dye bath, thereby simplifying the process for imparting a biocidal activity. It is also possible that the metallic ion is absorbed in pellets or powders of the ethylene copolymer, followed by drying, and then the metallic ion-containing ethylene copolymer is mixed with other resins for molding or processing.

The cationic polymer aqueous dispersion of the ethylene copolymer according to the present invention can be obtained, for example, by adding from 5 to 35 parts by weight of the ethylene copolymer pellets to 100 parts by weight of water, further adding thereto from 80 to 150 parts by mole of hydrochloric acid per 100 parts by mole of the amino group in the ethylene copolymer, stirring the mixture at 60° to 100° C. for 30 to 120 minutes, and adding from 80 to 150 parts by mole of an epihalohydrin compound ,per 100 parts by mole of the amino group in the ethylene copolymer, followed by stirring the mixture at 40° to 90° C. for 30 to 300 minutes.

When the ethylene copolymer, metallic ion-containing ethylene copolymer, or aqueous dispersion of the cationic polymer of the ethylene copolymer according to the present invention is used as an active ingredient of biocides, it may be used solely in the form of moldings, such as powders, pellets, films, sheets, and fibers, without being combined with any other components. If desired, it may be mixed with solid carriers, liquid carriers, surface active agents, and other adjuvants for preparations and formulated into various preparation forms, such as wettable powders, suspensions, dusts, and aqueous suspensions. The content of the active ingredient in these preparations usually ranges from about 0.1 to 95.0%, preferably from about 0.2 to 90%, by weight.

The solid carrier to be used includes fine powders or granules of kaolin clay, attapulgite clay, bentonite, acid clay, pyrophyllite, talc, diatomaceous earth, calcite, corncob, nutshell, urea, ammonium sulfate, and synthetic hydrous silicon hydroxide. The liquid carrier includes water.

The surface active agent to be used for emulsification, dispersion or wetting includes anionic surface active agents, e.g., alkylsulfates, alkyl- or arylsulfonates, dialkylsulfosuccinates, polyoxyethylene alkylaryl ethers, phosphates, and a naphthalenesulfonic acid-formalin condensate; and nonionic surface active agents, e.g., polyoxyethylene alkyl ethers, polyoxyethylene polyoxypropylene block copolymers, sorbitan fatty acid esters, and polyoxyethylene sorbitan fatty acid esters.

The adjuvants for preparations include lignin sulfonates, alginates, polyvinyl alcohol, gum arabic, carboxymethyl cellulose (CMC), and acid isopropyl phosphate (PAP).

When the ethylene copolymer, metallic ion-containing ethylene copolymer, or aqueous dispersion of the cationic polymer of the ethylene copolymer according to the present invention is used as an active ingredient of biocides, it is utilized as impregnated papers, paper diapers, wall papers, packaging material for clothing or food, air filters, sheets, constructional boards, mildewproofing coatings, and so on, either alone or in combination with a support, e.g., paper, plastics, and inorganic boards, in the form of liquids, emulsions, suspensions, pastes, granules, powders, films, porous films, sheets, fibers, molded articles or other forms in addition to the above-described preparations.

The ethylene copolymer or metallic ion-containing ethylene copolymer of the invention can be mixed with various thermoplastic resins, e.g., poly-α-olefins (e.g., polyethylene, polypropylene), chlorine-containing resins (e.g., polyvinyl chloride), polyesters, and polyamides, to provide a biocidal resin composition.

The resin composition according to the present invention can be processed to obtain stain-resistant, mildewproofing and biocidal resin products in the form of films (e.g., packaging films, trash bags), sheets (e.g., wall papers), molded articles (e.g., bathroom fittings, washing machine fittings, kitchen fittings), fibers, and the like.

The resin composition comprising the ethylene copolymer or metallic ion-containing ethylene copolymer and poly-α-olefins (e.g., polypropylene, polyethylene) or polyesters can be spun to obtain fibrous products. The fiber containing the ethylene copolymer or metallic ion-containing ethylene copolymer of the invention may be spun into fibrous products together with poly-α-olefin fibers, polyester fibers, polyamide fibers, acrylic fibers, and natural fibers. These fibrous products are utilized as deodorizing and biocidal clothing, such as deodorizing socks, or net products, such as fishing nets.

The ethylene copolymer r metallic ion-containing ethylene copolymer of the invention can further be combined with polypropylene resins, polyethylene resins, polyamide resins, etc. to obtain core-sheath or parallel conjugated fibers, which are processed into woven or non-woven fabric useful, for example, as filters of air conditioners, household goods (e.g., bedclothes), sanitary goods, and the like.

The present invention is now illustrated in greater detail with reference to the following Reference Examples, Preparation Examples, Test Examples and Examples, but it should be understood that the present invention is not deemed to be limited thereto. In these examples, all the percents and parts are by weight unless otherwise indicated.

REFERENCE EXAMPLES 1 TO 8

In a 2 l-volume autoclave type continuous reaction vessel equipped with a stirrer were continuously fed liquefied ethylene, a dialkylamino(meth)alkylacrylamide comonomer (as an 80% methanol solution), an ethylenically unsaturated comonomer, t-butyl peroxypivalate (as a 2% n-heptane solution) as a polymerization initiator, and methylcyclohexane as a chain transfer agent as shown in Table 1 below, and copolymerization was carried out under a pressure between 1,700 and 1,900 kg/cm$^2$ at a temperature between 170° and 90° C. as indicated in Table 1 to prepare ethylene copolymers (designated as EC-1 to EC-8).

The melt index (MI) of each of the resulting ethylene copolymers was measured according to JIS K-6760 (at 190° C.). The copolymerization ratio of ethylene/dimethylaminopropyl(meth)acrylamide/ethylenically unsaturated comonomer in the ethylene copolymer was determined by elemental analysis. The number average molecular weight of the ethylene copolymer was measured by GPC with a polystyrene sample whose molecular weight is known (produced by Tosoh Corporation) as a standard. The results of these determinations are shown in Table 1.

TABLE 1

|  | Ref. Ex. 1 | Ref. Ex. 2 | Ref. Ex. 3 | Ref. Ex. 4 | Ref. Ex. 5 | Ref. Ex. 6 | Ref. Ex. 7 | Ref. Ex. 8 |
|---|---|---|---|---|---|---|---|---|
| Sample No. | EC-1 | EC-2 | EC-3 | EC-4 | EC-5 | EC-6 | EC-7 | EC-8 |
| Copolymerization Condition: | | | | | | | | |
| Dialkylaminoalkyl-(meth)acrylamide (kg/hr) | DAPA[*1] (0.49) | DAPA (1.77) | DAPA (1.49) | DAPA (1.54) | DAPM[*2] (1.01) | DAPM (1.45) | DAPA (1.02) | DAPA (1.71) |
| Ethylenically unsaturated comonomer (kg/hr) | — | — | — | — | — | — | MMA[*3] (0.24) | DAM[*4] (0.10) |
| Ethylene feed (kg/hr) | 17.4 | 15.4 | 16.7 | 16.8 | 17.2 | 17.1 | 16.5 | 16.9 |
| Pressure (kg/cm$^2$) | 1700 | 1700 | 1700 | 1700 | 1700 | 1700 | 1700 | 1900 |
| Avg. Temperature (°C.) | 190 | 190 | 190 | 190 | 190 | 190 | 190 | 170 |
| Radical polymerization initiator (g/hr) | TBPP[*5] (2.5) | TBPP (7.7) | TBPP (8.7) | TBPP (8.9) | TBPP (8.1) | TBPP (9.0) | TBPP (8.7) | TBPP (10.1) |
| Chain transfer agent (kg/hr) | methyl-cyclo-hexane (1.61) | — | methyl-cyclo-hexane (1.19) | methyl-cyclo-hexane (1.37) | methyl-cyclo-hexane (1.50) | methyl-cyclo-hexane (1.21) | methyl-cyclo-hexane (1.61) | — |
| Ethylene Copolymer: | | | | | | | | |
| Yield (kg/hr) | 1.2 | 2.5 | 2.2 | 2.4 | 2.5 | 2.6 | 1.9 | 2.8 |
| Ethylene/(meth)acrylamide comonomer/ethylenically unsatd. comonomer (wt %) [mol %] | 82:18:0 [96.2: 3.8:0] | 50:50:0 [84.8: 15.2:0] | 65:35:0 [91.2: 8.8:0] | 59:41:0 [88.9: 11.1:0] | 72:28:0 [94.0: 6.0:0] | 61:39:0 [90.5: 9.5:0] | 58:32:10 [87.2: 8.6:4.2] | 50:45:5 [84.8: 13.7:1.5] |
| MI (g/10 min)[*6] | 108 | 55 | 280 | 300 | 96 | 270 | 415 | 52 |
| Number avg. mol. wt. (GPC) | 19100 | 32300 | 13200 | 10400 | 22600 | 11500 | 10100 | 31500 |

Note:
[*1] Dimethylaminopropylacrylamide
[*2] Dimethylaminopropylmethacrylamide
[*3] Methyl methacrylate
[*4] Dimethylaminoethyl methacrylate
[*5] t-Butyl peroxypivalate
[*6] According to JIS K-6760 (190° C.)

REFERENCE EXAMPLES 9 TO 12

In a 1,000 ml-volume glass flask were charged 360 g of water, 100 g of pellets of an ethylene copolymer comprising ethylene and a dialkylaminoalkyl(meth)acrylamide, and 36% hydrochloric acid in an amount of from 1.0 to 1.3 moles per mole of the amino group in the ethylene copolymer. The temperature of the mixture was elevated from room temperature to 100° C. over 30 minutes while stirring, and the stirring was continued at 100° C. for 60 minutes under refluxing, whereby the pellets were disintegrated to obtain a viscous slurry (solid-liquid mixture).

Subsequently, the slurry was cooled to 80° while stirring, and epichlorohydrin was added thereto dropwise over 30 minutes in an amount of from 1.0 to 1.5 moles per mole of the amino group in the ethylene copolymer. The stirring was continued at 80° C. for an additional period of 270 minutes to obtain pale brown uniform aqueous dispersions of cationic polymer (designated as S-1 to S-4). The pH at 25° C., the viscosity at 25° C, and the solids content of the aqueous dispersion were as shown in Table 2. The solids content was measured by heating the aqueous dispersion in hot air at 100° C. to vaporize the water content and weighing the residue.

TABLE 2

|  | Ref. Ex. 9 | Ref. Ex. 10 | Ref. Ex. 11 | Ref. Ex. 12 |
|---|---|---|---|---|
| Sample No. | S-1 | S-2 | S-3 | S-4 |
| Ethylene Copolymer: | | | | |
| Dialkylaminoalkyl(meth)acrylamide comonomer (wt %) | DAPA[*1] (41) | DAPA (50) | DAPM[*2] (39) | DAPM (28) |
| MI (g/10 min) | 300 | 55 | 270 | 96 |
| Cationic Polymer: | | | | |
| Hydrochloric acid (molar ratio to amino group) | 1.0 | 1.3 | 1.0 | 1.2 |
| Epichlorohydrin (molar ratio to amino group) | 1.0 | 1.5 | 1.0 | 1.2 |
| Aqueous Dispersion: | | | | |
| Solids content (wt %) | 26 | 27 | 22 | 17 |
| pH | 5.6 | 6.7 | 6.5 | 6.7 |
| Viscosity (cps) | 49 | 35 | 31 | 84 |
| Uniformity | good | good | good | good |

Note:
[*1] Dimethylaminopropylacrylamide
[*2] Dimethylaminopropylmethacrylamide

REFERENCE EXAMPLE 13

In the same reaction vessel as used in Reference Example 1 were continuously fed liquefied ethylene, dimethylaminoethyl methacrylate as a comonomer, and t-butyl peroxypivalate (as a 2% n-heptane solution) as a polymerization initiator, and copolymerization was effected under a pressure of 1,900 kg/cm$^2$ at a temperature of 170° C. to obtain an ethylene copolymer.

The resulting ethylene copolymer had a melt index of 290 g/10 min as measured in accordance with JIS K-6760 at 190° C., and the copolymerization ratio of dimethylaminoethyl methacrylate was found to be 43% (corresponding to 12 mol %) by elemental analysis.

PREPARATION EXAMPLE 1

Each of the ethylene copolymers EC-1 to EC-4 as prepared in Reference Examples 1 to 4 was pulverized under freezing to obtain a resin powder having an average particle size of 100 μm. Ten parts of the resin powder, 3 parts of calcium lignin sulfonate, 2 parts of sodium lauryl sulfate, 45 parts of synthetic hydrous silicon hydroxide, and 40 parts of kaolin clay were thoroughly mixed to prepare a 10% wettable powder of EC-1, EC-2, EC-3, or EC-4, respectively.

PREPARATION EXAMPLE 2

Each of the ethylene copolymers EC-5 to EC-8 as prepared in Reference Examples 5 to 8 was pulverized under freezing to obtain a resin powder having an average particle size of 100 μm. Two parts of the resin powder, 88 parts of kaolin clay, and 10 parts of talc were thoroughly mixed to obtain a 2% wettable powder of EC-5, EC-6, EC-7, or EC-8, respectively The biocidal activity of the ethylene copolymer of the present invention and the aqueous dispersion of the cationic polymer thereof was evaluated in the following Test Examples.

TEST EXAMPLE 1

Antimicrobial Spectrum on Phytopathogenic Microorganism

Each of the 10% wettable powder of EC-1, 10% wettable powder of EC-4, and S-1 was added to a potato-sucrose agar (PSA) medium at a concentration of active ingredient of 10,000 ppm. The mixture was poured into a petri-dish of 9 cm in diameter and gelled. A cell suspension, a spore suspension, or a mycelial disc of microorganism was inoculated to the center of the medium plate and incubated at 25° C.

The growth of the microorganism was observed, and a growth inhibitory effect was evaluated according to the following rating system. The results obtained are shown in Table 3.
4: 100% growth inhibition
3: 90% or more growth inhibition
2: 60% to 89% growth inhibition
1: 60% or less growth inhibition

TABLE 3

| Test Bacterium | Sample No. | | |
|---|---|---|---|
| | EC-1 | EC-4 | S-1 |
| Agrobacterium tumefaciens | 2 | 4 | 4 |
| Erwinia carotovora | 2 | 3 | 4 |
| Pseudomonas lachrymans | 2 | 4 | 4 |
| Pseudomonas syringae | 2 | 4 | 4 |
| Xanthomonas citri | 2 | 3 | 4 |
| Alternaria radicina | 1 | 1 | 2 |
| Pyricularia oryzae | 1 | 1 | 2 |
| Cochliobolus miyabeanus | 1 | 1 | 2 |
| Rhizocionia solani | 1 | 1 | 2 |
| Gibberella fujikuroi | 1 | 1 | 2 |
| Pseudocercosporella herpotrichoides | 1 | 1 | 2 |
| Rhynchosporium secalis | 1 | 1 | 2 |
| Septoria tritici | 1 | 1 | 2 |
| Pyrenophora graminea | 1 | 1 | 2 |
| Penicillium digitatum | 1 | 1 | 2 |

TABLE 3-continued

| Test Bacterium | Sample No. | | |
|---|---|---|---|
| | EC-1 | EC-4 | S-1 |
| Sclerotinia mali | 1 | 1 | 2 |
| Valsa mali | 1 | 1 | 2 |
| Venturia inaequalis | 1 | 1 | 2 |
| Aspergillus glaucus | 2 | 2 | 3 |
| Aspergillus niger | 2 | 1 | 2 |
| Aureobasidium pullulans | 1 | 1 | 2 |
| Chaetomium glubosum | 1 | 2 | 3 |
| Cladosporium herbarum | 1 | 2 | 3 |
| Fusarium moniliforme | 1 | 1 | 2 |
| Mucor spinescens | 1 | 1 | 2 |
| Penicillium citrinum | 1 | 1 | 2 |
| Bacillus subtilius | 2 | 4 | 4 |
| Enterobacter aerogens | 2 | 4 | 4 |
| Pseudomonas aeruginosa | 2 | 4 | 4 |
| Saccharomyces cerevisiae | 4 | 2 | 3 |
| Candida tropicalis | 2 | 2 | 3 |

TEST EXAMPLE 2

Antimicrobial Activity on Direct Contact with Bacterium

The antimicrobial activity of the ethylene copolymer or the aqueous dispersion of its cationic polymer was evaluated as follows. Under the condition used in this test, resin materials are often brought into direct contact with bacteria.

Test Bacterium: *Pseudomonas syringae*
Medium: PG medium (comprising 2 g of polypeptone, 5 g of glucose, and 1 l of water)
Test Method:

An aqueous suspension of each of EC-2, 3, and 5 to 8 and S-2 to 4 was suspended in a PG medium to a prescribed concentration, and $10^6$ cells of the test bacterium were inoculated thereto per milliliter and cultured at 27° C. for about 20 hours by shaking culture. The growth inhibition (%) was obtained from absorbance measured by means of a spectrophotometer. The results obtained are shown in Table 4 below.

TABLE 4

| Sample No. | Concn. of Sample (ppm) | Absorbance | Percent Inhibition (%) |
|---|---|---|---|
| EC-2 | 1000 | 0.000 | 100 |
| EC-3 | 1000 | 0.000 | 100 |
| " | 500 | 0.031 | 91 |
| EC-5 | 1000 | 0.011 | 99 |
| EC-6 | 1000 | 0.000 | 100 |
| EC-7 | 1000 | 0.000 | 100 |
| " | 500 | 0.024 | 98 |
| EC-8 | 1000 | 0.000 | 100 |
| S-2 | 1000 | 0.000 | 100 |
| S-3 | 1000 | 0.000 | 100 |
| " | 500 | 0.000 | 100 |
| S-4 | 1000 | 0.009 | 99 |
| Comparative Sample* | 10000 | 0.890 | 0 |
| | 1000 | 0.893 | 0 |
| | 500 | 0.891 | 0 |
| Control** (untreated) | — | 0.892 | 0 |

Note:
*A sample prepared in the same manner as in Preparation Example 1 but using the ethylene copolymer prepared in Reference Example 13.
**Only the PG medium.

REFERENCE EXAMPLE 14

Ethylene copolymers of Table 5 below were prepared in the same manner as in Reference Examples 1 to 8.

TABLE 5

|  | Sample No. | | | | | | |
|---|---|---|---|---|---|---|---|
|  | A | B | C | D | E | F | G |
| Monomers (wt %): | | | | | | | |
| Ethylene | 56 | 72 | 82 | 65 | 67 | 90 | 45 |
| Dimethylamino propylacrylamide | 44 | 28 | 18 | — | 25 | 10 | 55 |
| Dimethylamino propylmethacrylamide | — | — | — | 35 | — | — | — |
| Dimethylamino ethyl methacrylate | — | — | — | — | 8 | — | — |
| Number Average Molecular Weight* | 28000 | 32000 | 19100 | 11500 | 17400 | 45000 | 9200 |

Note:
*Measured by GPC on a polystyrene standard

EXAMPLE 1

Each of Samples A to E as prepared in Reference Example 14 was kneaded with various resins in an extruder having a diameter of 30 mm (L/D=20) under the conditions shown in Table 6 below, to obtain 5 kg of pellets.

The pellets were supplied to a spinning machine comprising an extruder having a diameter of 25 mm (L/D=15) having, at the output end thereof, a spinning nozzle having 12 orifices each having a diameter of 0.8 mm, melt-spun under conditions of 1 kg/hr in extrusion rate and 450 m/min in take-up rate at a temperature shown in Table 6, and stretched three times while running on a hot plate to obtain multifilament samples having a fineness of 10 denier/filament (designated as F-1 to F-7).

TABLE 6

|  | Sample No. | | | | | | |
|---|---|---|---|---|---|---|---|
|  | F-1 | F-2 | F-3 | F-4 | F-5 | F-6 | F-7 |
| Composition (part): | | | | | | | |
| Ethylene Copolymer | A (4) | B (4) | B (6) | C (10) | C (10) | D (4) | E (2) |
| Thermoplastic Resin* | R-1 (100) | R-1 (100) | R-1 (100) | R-2 (100) | R-3 (100) | R-4 (100) | R-5 (100) |
| Kneading Temperature (°C.) | 210 | 210 | 210 | 270 | 270 | 280 | 280 |
| Spinning Temperature (°C.) | 210 | 210 | 210 | 270 | 270 | 280 | 280 |

Note:
*R-1: Noblen ® FL-800 (a trade name for polypropylene having an MFR of 10 g/10 min, produced by Sumitomo Chemical Co., Ltd.)
R-2: A1030 BRL (a trade name for polyamide-6, produced by Unitika Ltd.)
R-3: Maranyl ® A-125 (a trade name for polyamide-66, produced by ICI Inc.)
R-4: MA 2103 (a trade name for polyethylene terephthalate, produced by Unitika Ltd.)
R-5: TUFPET ® N1200 (a trade name for polybutylene terephthalate, produced by Mitubishi Rayon Co., Ltd.)

EXAMPLE 2

Ten grams of each of Samples F-1 to F-7 was immersed in 300 ml of an aqueous solution of a metal salt shown in Table 7 at 60° C. for 30 minutes to adsorb the metallic ion on the filaments. The sample was thoroughly washed with deionized water and dried at 50° C. for 6 hours. Then, the sample was dyed with an acid dye Suminol ® Fast Blue PR conc (produced by Sumitomo Chemical Co., Ltd.) at a pH of from 3 to 5 at a temperature of 100° C. for 30 minutes. The dyed samples were designated as D-1 to D-14. For reference, filaments having no metallic ion adsorbed thereon were similarly dyed (designated as D-15).

A part of the resulting dyed sample was repeatedly washed with a 1 g/l solution of a detergent Kao Attack ® (a trade name, produced by Kao Corporation) at 50° C. for 10 minutes.

The metallic ion contents in the sample before dyeing and before and after the washing were measured by atomic-absorption spectroscopy after ashing and dissolving with an acid and, as a result, it was revealed that the metallic ion was substantially retained even after washing with a detergent. The results are shown in Table 7.

TABLE 7

|  | Dyed Sample No. | | | | | | |
|---|---|---|---|---|---|---|---|
|  | D-1 | D-2 | D-3 | D-4 | D-5 | D-6 | D-7 |
| Filament | F-1 | F-2 | F-2 | F-2 | F-2 | F-2 | F-2 |
| Metal Salt | $CuSO_4$ | $CuSO_4$ | $CuSO_4$ | $CuSO_4$ | $CuSO_4$ | $AgNO_3$ | $AgNO_3$ |
| Metallic Ion Concn. (wt %) | 0.5 | 0.002 | 0.0002 | 0.0002 | 0.0002 | 0.002 | 0.0002 |
| Metal Content in Filament Before Dyeing (wt %) | 3.7 | 0.033 | 0.006 | 0.006 | 0.006 | 0.042 | 0.006 |
| Metal Content After Dyeing (wt %) | 3.6 | 0.032 | 0.006 | 0.006 | 0.006 | 0.040 | 0.006 |
| Washing | 1 | 1 | 1 | 20 | 50 | 1 | 1 |

TABLE 7-continued

| Times Metal Content After washing (wt %) | 3.6 | 0.031 | 0.005 | 0.005 | 0.004 | 0.039 | 0.005 |
|---|---|---|---|---|---|---|---|

| | D-8 | D-9 | D-10 | D-11 | D-12 | D-13 | D-14 | D-15 |
|---|---|---|---|---|---|---|---|---|
| Filament | F-2 | F-2 | F-3 | F-4 | F-5 | F-6 | F-7 | F-2 |
| Metal Salt | AgNO$_3$ | ZnSO$_4$ | CuSO$_4$ | CuSO$_4$ | CuSO$_4$ | CuSO$_4$ | CuSO$_4$ | — |
| Metallic Ion Concn. (wt %) | 0.0002 | 0.002 | 0.002 | 0.002 | 0.002 | 0.002 | 0.002 | — |
| Metal Content in Filament Before Dyeing (wt %) | 0.006 | 0.030 | 0.037 | 0.026 | 0.029 | 0.023 | 0.024 | — |
| Metal Content After Dyeing (wt %) | 0.006 | 0.028 | 0.036 | 0.025 | 0.027 | 0.023 | 0.023 | — |
| Washing Times | 50 | 1 | 1 | 1 | 1 | 1 | 1 | 1 |
| Metal Content After washing (wt %) | 0.004 | 0.028 | 0.035 | 0.024 | 0.026 | 0.022 | 0.022 | — |

TEST EXAMPLE 3

Antimicrobial Activity on Fungus

The antimicrobial activity of the dyed samples D-1 to D-15 to a fungus was evaluated as follows.

Test Fungus:

*Cladosporium herbarum, Rhizopus nigricans,* and *Trichoderma sp.*

Test Method:

One gram of each of the samples was placed into a petri-dish. A suspension of spores of the test fungus in an aqueous solution of inorganic salts (comprising 0.7 g of KH$_2$PO$_4$, 0.7 g of K$_2$HPO$_4$, 0.7 g of MgSO$_4$.7H$_2$O, 1.0 g of NH$_4$NO$_3$, 0.005 g of NaCl, 0.001 g of MnSO$_4$.7H$_2$O, 0.002 g of FeSO$_4$.7H$_2$O, 0.002 g of ZnSO$_4$.7H$_2$O, and 1 l of water) was spray-inoculated to the sample and incubated at 27° C. and at a high humidity for one month. The growth of the fungus was observed and evaluated according to the following rating system. The results obtained are shown in Table 8.

+++: Growth of the fungus was observed on the half or more of the sample.

++: Growth of the fungus was observed on the quarter to half of the sample.

+: Growth of the fungus was observed on about the quarter of the sample.

±: Slight growth of the fungus was observed on the sample.

—: No growth of the fungus was observed on the sample.

TABLE 8

| Sample No. | Growth of Fungus |
|---|---|
| D-1 | — |
| D-2 | — |
| D-3 | ± |
| D-4 | ± |
| D-5 | ± |
| D-6 | — |
| D-7 | ± |
| D-8 | ± |
| D-9 | + |
| D-10 | — |
| D-11 | — |

TABLE 8-continued

| Sample No. | Growth of Fungus |
|---|---|
| D-12 | — |
| D-13 | — |
| D-14 | — |
| D-15 | + |
| Control* | +++ |

Note: *Polypropylene fiber

TEST EXAMPLE 4

Antimicrobial Activity on Bacterium

The antimicrobial activity of the dyes samples D-1 and D-6 on *Pseudomonas stringae* was evaluated as follows.

Each sample was suspended in a PG medium in a prescribed concentration, and the test bacterium (10$^6$ cells/ml) was inoculated to the medium and shake-cultured at 27° C. for about 20 hours. The culture was filtered through a filter paper, and the turbidity was measured with a spectrophotometer to evaluate the degree of growth inhibition (%). The results obtained are shown in Table 9.

TABLE 9

| Sample No. | Sample Concn. (%) | Absorbance $(O.D._{590})$ | Percent Inhibition (%) |
|---|---|---|---|
| D-1 | 10 | 0.00 | 100 |
| D-1 | 1 | 0.00 | 100 |
| D-6 | 10 | 0.00 | 100 |
| Control* | 10 | 0.85 | 0 |

Note: *Polypropylene fiber

TEST EXAMPLE 5

Antimicrobial Activity on Fungus

The antimicrobial activity to fungi of Samples F-1 to F-7 prepared in Example 1 was determined in the same manner as in Test Example 3. The results obtained are shown in Table 10.

Table 10 also shows the results obtained with respect to a comparative sample containing only the thermoplastic resin (R-1).

TABLE 10

| | Sample No. | | | | | | | |
|---|---|---|---|---|---|---|---|---|
| | T-1 | T-2 | T-3 | T-4 | T-5 | T-6 | T-7 | Comp. |
| Resin Composition (part): | | | | | | | | |
| Ethylene Copolymer | B (4) | B (10) | B (4) | B (4) | F (40) | G (10) | B (0.5) | — |
| Thermoplastic Resin* | R-1 (100) | R-1 (100) | R-2 (100) | R-4 (100) | R-1 (100) | R-1 (100) | R-1 (100) | R-1 (100) |
| Copper Content (wt %) | 0.006 | 0.017 | 0.005 | 0.005 | 0.025 | 0.002 | 0 | — |
| Growth of Fungus | ± | − | ± | ± | − | + | + | +++ |

Note: *R-1, R-2, and R-4 are as specified in the footnote of Table 6.

As demonstrated in the foregoing test examples, the antimicrobial resin composition according to the present invention exhibits excellent antimicrobial activity on various harmful microorganisms and is therefore useful as an active ingredient of antimicrobial preparations as well as mildewproofing, stain-resistant, and antimicrobial resin products.

While the invention has been described in detail and with reference to specific embodiments thereof, it will be apparent to one skilled in the art that various changes and modifications can be made therein without departing from the spirit and scope thereof.

What is claimed is:

1. A method for controlling harmful microorganisms which comprises applying to the vicinity of said microorganisms an antimicrobial substance containing, as an active ingredient, an ethylene copolymer comprising from 45 to 85% by weight of ethylene, from 15 to 55% by weight of at least one dialkylaminoalkylacrylamide comonomer represented by formula (I):

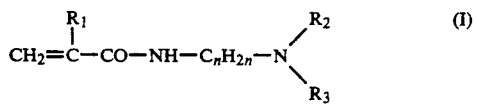

wherein $R_1$ represents a hydrogen atom or a methyl group; $R_2$ and $R_3$, which may be the same or different, each represents an alkyl group having from 1 to 4 carbon atoms; and n represents an integer of from 2 to 5, and up to 20% by weight of one or more of other ethylenically unsaturated comonomers selected from the group consisting of methyl acrylate, ethyl acrylate, methyl methacrylate, vinyl acetate, dimethylaminoethyl methacrylate, and dimethylaminoethyl acrylate, said ethylene copolymer having a number average molecular weight of from 5,000 to 50,000.

2. A method for controlling harmful microorganisms which comprises applying to the vicinity of said microorganisms an antimicrobial resin composition comprising 100 parts by weight of a thermoplastic resin and from 0.1 to 50 parts by weight of an ethylene copolymer comprising from 45 to 85% by weight of ethylene, from 15 to 55% by weight of at least one dialkylaminoalkylacrylamide comonomer represented by formula (I):

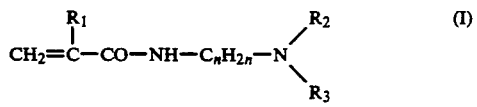

wherein $R_1$ represents a hydrogen atom or a methyl group; $R_2$ and $R_3$, which may be the same or different, each represents an alkyl group having from 1 to 4 carbon atoms; and n represents an integer of from 2 to 5, and up to 20% by weight of one or more of other ethylenically unsaturated comonomers selected from the group consisting of methyl acrylate, ethyl acrylate, methyl methacrylate, vinyl acetate, dimethylaminoethyl methacrylate, and dimethylaminoethyl acrylate, said ethylene copolymer having a number average molecular weight of from 5,000 to 50,000.

3. A method as claimed in claim 1, wherein said ethylene copolymer is in the form of an aqueous dispersion of a cationic polymer which is obtained by reacting the ethylene copolymer with hydrochloric acid in water to form a quaternary salt and then addition-reacting the quaternary salt with an epihalohydrin.

4. A method as claimed in claim 2, wherein said ethylene copolymer is in the form of an aqueous dispersion of a cationic polymer which is obtained by reacting the ethylene copolymer with hydrochloric acid in water to form a quaternary salt and then addition-reacting the quaternary salt with an epihalohydrin.

5. A method as claimed in claim 1, wherein said ethylene copolymer contains a metallic ion.

6. A method as claimed in claim 2, wherein said ethylene copolymer contains a metallic ion.

7. A method as claimed in claim 5, wherein said metallic ion is at least one of the following: a silver ion, a copper ion, or a zinc ion.

8. A method as claimed in claim 6, wherein said metallic ion is at least one of the following: a silver ion, a copper ion, or a zinc ion.

* * * * *